United States Patent
Sattler

(10) Patent No.: US 9,101,271 B2
(45) Date of Patent: Aug. 11, 2015

(54) DEVICE AND PROCESS FOR DETERMINING THE BODY CORE TEMPERATURE

(75) Inventor: Frank Sattler, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 590 days.

(21) Appl. No.: 13/474,190

(22) Filed: May 17, 2012

(65) Prior Publication Data
US 2013/0085708 A1    Apr. 4, 2013

(30) Foreign Application Priority Data
Sep. 30, 2011   (DE) .......................... 10 2011 114 620

(51) Int. Cl.
*G06F 15/00*   (2006.01)
*A61B 5/01*   (2006.01)
*G01K 1/20*   (2006.01)
(Continued)

(52) U.S. Cl.
CPC . *A61B 5/01* (2013.01); *G01K 1/165* (2013.01); *G01K 1/20* (2013.01); *G01K 7/427* (2013.01); *A61B 2562/0271* (2013.01)

(58) Field of Classification Search
CPC ......... G01K 13/002; G01K 7/42; G01K 1/02; G01K 1/026; A61B 5/01; A61B 5/0008; A61B 5/015; G01J 5/02; G01J 5/025; G06F 1/206
USPC ............ 702/131, 130, 132, 134, 99; 600/549; 340/870.17; 374/133, E13.002, 121, 374/170
See application file for complete search history.

(56) References Cited

U.S. PATENT DOCUMENTS 7,299,090 B2 *  11/2007  Koch ............................. 600/547
2006/0173375 A1    8/2006  Koch
2007/0055171 A1    3/2007  Fraden
(Continued)

FOREIGN PATENT DOCUMENTS

CN           101843476 A    9/2010
DE    10 2005 004 933 B3    8/2006
(Continued)

*Primary Examiner* — John Breene
*Assistant Examiner* — Mohammad K Islam
(74) *Attorney, Agent, or Firm* — McGlew and Tuttle, P.C.

(57) ABSTRACT

A device for determining the body core temperature of a living being includes a first temperature sensor (15) for detecting the skin temperature $T_1$, an insulator (11) for receiving the first temperature sensor (15), a second temperature sensor (17) in the insulator (11) for detecting a temperature $T_2$ and a third temperature sensor (19), which is arranged opposite the first temperature sensor (15) at the insulator (11), for detecting a temperature $T_3$ near the environment. Assuming a constant ratio of lateral heat fluxes α at the insulator (11) between the temperature sensors (15, 17, 29), the body core temperature $T_{core}$ is determined by the relationship described by the formula $$T_{core} = T_1 \cdot \left[1 + \frac{k_s}{k_g}\left(1 + \frac{1}{\alpha}\right)\right] - T_2 \cdot \left(\frac{k_s}{k_g} + \frac{k_s + k_t}{\alpha k_g}\right) + T_3 \cdot \frac{k_t}{\alpha k_g}$$

in which
$k_g$=heat transfer coefficient of the tissue and
$k_s$, $k_t$=heat transfer coefficients of the insulator (11).

12 Claims, 4 Drawing Sheets

(51) Int. Cl.
*G01K 1/16* (2006.01)
*G01K 7/42* (2006.01)

(56) References Cited

U.S. PATENT DOCUMENTS

2007/0295713 A1* 12/2007 Carlton-Foss ............... 219/497
2008/0170600 A1 7/2008 Sattler et al.
2011/0317737 A1* 12/2011 Klewer et al. ................ 374/29
2012/0109571 A1* 5/2012 Shimizu ....................... 702/130

FOREIGN PATENT DOCUMENTS

DE   10 2006 012 338 B3   7/2007
DE   10 2007 002 369 B3   5/2008

* cited by examiner

DEVICE AND PROCESS FOR DETERMINING THE BODY CORE TEMPERATURE

CROSS REFERENCE TO RELATED APPLICATIONS

This application claims the benefit of priority under 35 U.S.C. §119 of German Patent Application DE 10 2011 114 620.6 filed Sep. 30, 2011, the entire contents of which are incorporated herein by reference.

FIELD OF THE INVENTION

The present invention pertains to a device and a process for determining the body core temperature of a living being.

BACKGROUND OF THE INVENTION

The body core temperature is of special interest when measuring the inner temperature of objects, especially of the human body. Fields of application are medical engineering during the monitoring of adults, children and newborns in the intensive care unit and safety engineering, in general, personal safety and for members of firefighter teams.

A device of this type is known from DE 10 2005 004 933 B3 (corresponding to U.S. Pat. No. 7,299,090). In the prior-art device, the temperature of the skin surface is measured with a first temperature sensor, and a second temperature sensor, which is arranged at a spaced location from the first temperature sensor via a heat insulation, detects the temperature near the environment. Taking the heat transfer coefficient of the tissue of the living being and the heat transfer coefficient of the insulation into account, the body core temperature of the living being can be calculated from the measured temperatures. The idealized formula for the calculation is based on the assumption that the heat flux released by the skin surface onto the temperature-measuring device is sent completely from the first temperature sensor to the second temperature sensor.

By combining the skin temperature with the heat flux, which is obtained from the difference of the two temperatures, the body core temperature $T_{core}$ is then calculated as:

$$T_{core} = T_1 + \frac{k_s}{k_g}(T_1 - T_2) = T_1 \cdot \left(1 + \frac{k_s}{k_g}\right) + T_2 \cdot \frac{k_s}{k_g} \quad (1)$$

Here, $T_1$ denotes the temperature of the first temperature sensor near the body and $T_2$ the temperature of the second temperature sensor away from the body. Factor $k_s$ is the heat transfer coefficient of the insulator between the temperature sensors and $k_g$ is the heat transfer coefficient of the human tissue between the body core and the first temperature sensor near the body. The two temperatures of the first and second temperature sensors are linked with one another linearly in the formula.

A heat flux due to energy loss, which is released to the sensor housing of the temperature-measuring device, does additionally occur in a real system. To take the heat flux due to energy loss into account, a marginal temperature sensor is provided, which is arranged in the area of the outer wall of the sensor housing and detects the marginal temperature of the sensor housing at the transition to the environment. The taking into account of the heat flux due to energy loss leads in the formula used for the calculation to a compensation term, which depends on the measured marginal temperature. The drawback of this is that the marginal temperature sensor can detect the marginal temperature only locally and effects from the environment may distort the measurement. The problem is compounded by time-dependent environmental effects, which lead to a time-dependent correction.

SUMMARY OF THE INVENTION

A basic object of the present invention is to provide an improved device and a corresponding process for measured value correction in a temperature-measuring device of the type mentioned.

Provisions are made according to the present invention for a temperature sensor for detecting the heat flux due to energy loss to be arranged within the insulator such that it is located in the area of the main heat flux. As a result, the effects of the environment on the measured temperature value measured with the additional temperature sensor are minimized.

The temperature-measuring device according to the present invention comprises a first temperature sensor for measuring temperature $T_1$ in a position near the body, a third temperature sensor for measuring temperature $T_3$ in a position near the environment, and a second temperature sensor between the first and third temperature sensors for detecting a temperature $T_2$ within the insulator.

The determination of a compensation term for the calculation of the body core temperature is based on the consideration that the area between the first temperature sensor and the second temperature sensor can be considered to be a first double temperature sensor and the area between the second temperature sensor and the third temperature sensor is a second double temperature sensor. The prerequisite is that the second temperature sensor be located in the area of the main heat flux. The main heat flux extends from the body tissue via the first temperature sensor into the insulator to the second temperature sensor and via the insulator to the third temperature sensor. Furthermore, it is assumed that the lateral heat fluxes due to energy loss $Q_4$ and $Q_5$ of the first double temperature sensor and of the second double temperature sensor are at a fixed ratio to one another, and the absolute heat fluxes due to energy loss are not needed.

Assuming a constant ratio of the lateral heat fluxes due to energy loss, $Q_5/Q_4=\alpha$, the following relationships can be stated for the first and second double temperature sensors:

$$(T_{core}-T_1) \cdot k_g = Q_4 + (T_1-T_2) \cdot k_s$$

$$(T_1-T_2) \cdot k_s = \alpha \cdot Q_4 + (T_2-T_3) \cdot k_t \quad (2)$$

Here, $k_t$ is the coefficient of thermal conductivity of the insulator between the second and third temperature sensors.

The unknown $Q_4$ can be eliminated in this equation and Equations (2) can then be solved for $T_{core}$ as follows:

$$T_{core} = T_1 \cdot \left[1 + \frac{k_s}{k_g}\left(1+\frac{1}{\alpha}\right)\right] - T_2 \cdot \left(\frac{k_s}{k_g} + \frac{k_s+k_t}{\alpha k_g}\right) + T_3 \cdot \frac{k_t}{\alpha k_g} \quad (3)$$

The body core temperature $T_{core}$ is a function of three measured temperatures $T_1$, $T_2$ and $T_3$ as well as of constant factors $k_s$, $k_g$, $k_t$ and $\alpha$.

The insulator between the temperature sensors may consist of different materials, but it may also be manufactured from a homogeneous block with mounting holes for the temperature sensors.

The process for determining the body core temperature of a living being is carried out with a measuring device which has temperature sensors on both sides of an insulator for detecting a temperature $T_1$ near the body and a temperature $T_3$ away from the body, and a temperature sensor within the insulator for detecting a temperature $T_2$, wherein a main heat flux extends from the body tissue into the insulator and from the temperature sensor near the body to the temperature sensor away from the body, and lateral heat fluxes $Q_4$, $Q_5$ are present between the temperature sensors.

The process is characterized by the steps of arranging the temperature sensor for detecting the temperature $T_2$ in the area of the main heat flux within the insulator between the outer temperature sensors, and, assuming a constant ratio of the lateral heat fluxes $Q_5/Q_4 = \alpha$ between two respective adjacent temperature sensors, of determining the body core temperature $T_{core}$ from the relationship described by the formula $$T_{core} = T_1 \cdot \left[1 + \frac{k_s}{k_g}\left(1 + \frac{1}{\alpha}\right)\right] - T_2 \cdot \left(\frac{k_s}{k_g} + \frac{k_s + k_t}{\alpha k_g}\right) + T_3 \cdot \frac{k_t}{\alpha k_g}$$

in which $k_g$=heat transfer coefficient of the tissue and $k_s$, $k_t$=heat transfer coefficients of the insulator between the temperature sensors.

An exemplary embodiment of the present invention is shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
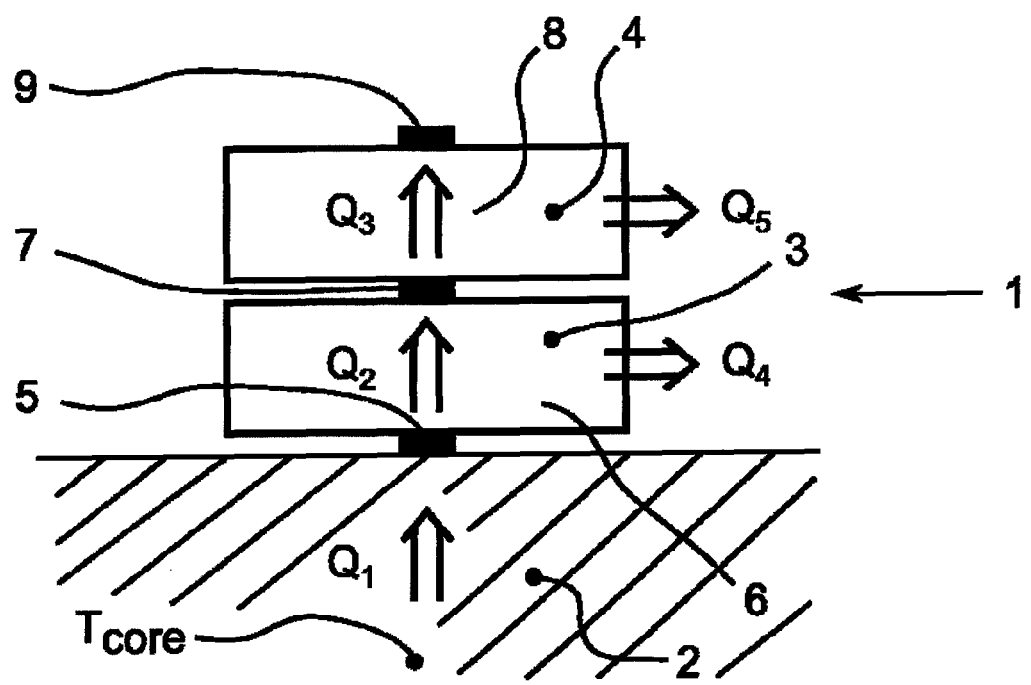
FIG. 1 is a schematic partially sectional view of a temperature-measuring device according to the present invention.

Referring to the drawings in particular, FIG. 1 schematically illustrates a temperature-measuring device 1 for determining the body core temperature $T_{core}$. The first temperature-measuring device 1 is located on the surface of the body tissue 2 and comprises, in a serial arrangement, a first double temperature sensor 3 and a second double temperature sensor 4. The first double temperature sensor 3 has a first temperature sensor 5 for detecting the temperature $T_1$ near the body at the surface of the body tissue 2 and, spaced by a first insulator 6, a second temperature sensor 7 for temperature $T_2$. The second double temperature sensor 4 comprises a second temperature sensor 7, a second insulator 8 and a third temperature sensor 9 for measuring the temperature $T_3$ near the environment. $Q_1$ is the heat flux within the body tissue 2 between $T_{core}$ and the first temperature sensor 5 with the heat transfer coefficient $k_g$.

$Q_2$ is the main heat flux within the first double temperature sensor 3 between the first temperature sensor 5 and the second temperature sensor 7, and $Q_3$ is the main heat flux within the second double temperature sensor 4 between the second temperature sensor 7 and the third temperature sensor 9. The lateral, interfering heat fluxes are $Q_4$ for the first double temperature sensor 3 and $Q_5$ for the second double temperature sensor 4. A constant ratio $\alpha$ of $Q_5/Q_4$ is assumed. $k_s$ is the heat transfer coefficient of the first double temperature sensor 3 and $k_t$ is the heat transfer coefficient of the second double temperature sensor 4. A typical value of 0.25 is obtained for $\alpha$. $k_g$ is typically about 45 W/m²K $k_s$ and $k_t$ equals about 70 W/m²K. However, it is also possible that the values for $k_s$ and $k_t$ are identical.

Figure 2:
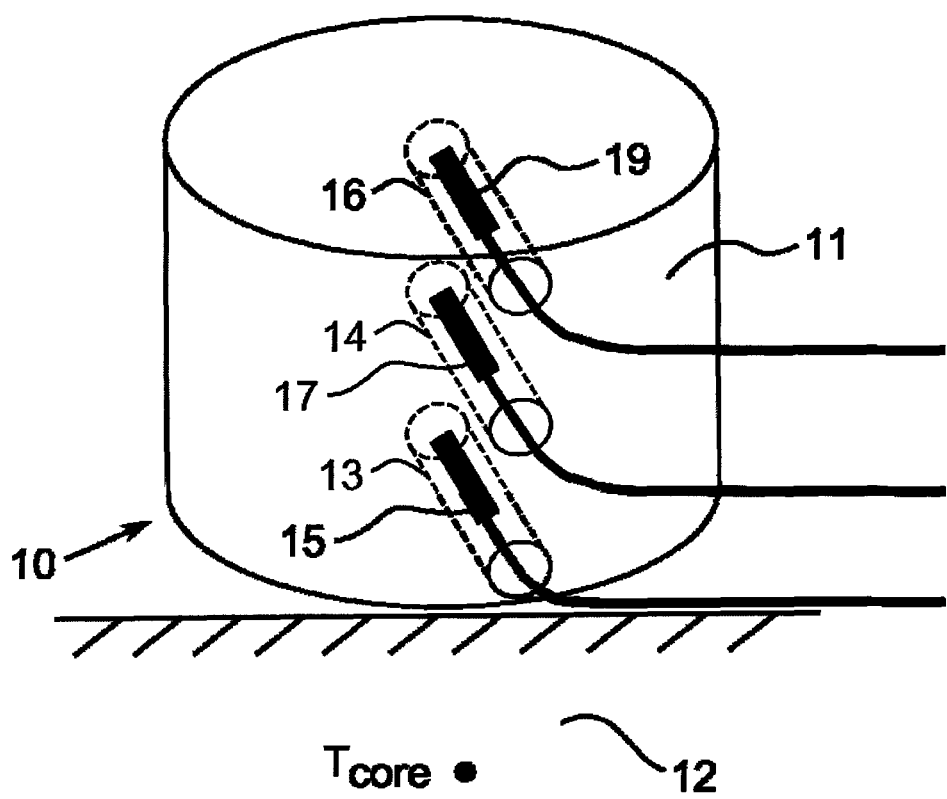
FIG. 2 is a schematic perspective and partially sectional view showing a first embodiment of the temperature-measuring device according to the invention.

FIG. 2 shows a first temperature-measuring device 10 with a cylindrical insulator 11, with a first temperature sensor 15 on the underside, which lies on the surface of a body tissue 12, with a second temperature sensor 17 in the middle and with a third temperature sensor 19 on the top side for measuring the temperature near the environment. Insulator 11 has a diameter of about 10 mm and a height of 8-10 mm. It consists of a homogeneous material with a thermal conductivity between 0.05 and 0.3 W/mK. Insulator 11 has mounting holes 13, 14, 16 for the temperature sensors 15, 17, 19. Suitable materials for insulator 11 are polyethylene (PE), polyether ether ketone (PEEK), polymethyl methacrylate (PMMA) as well as closed-cell, porous or foam-like insulating materials.

Figure 3:
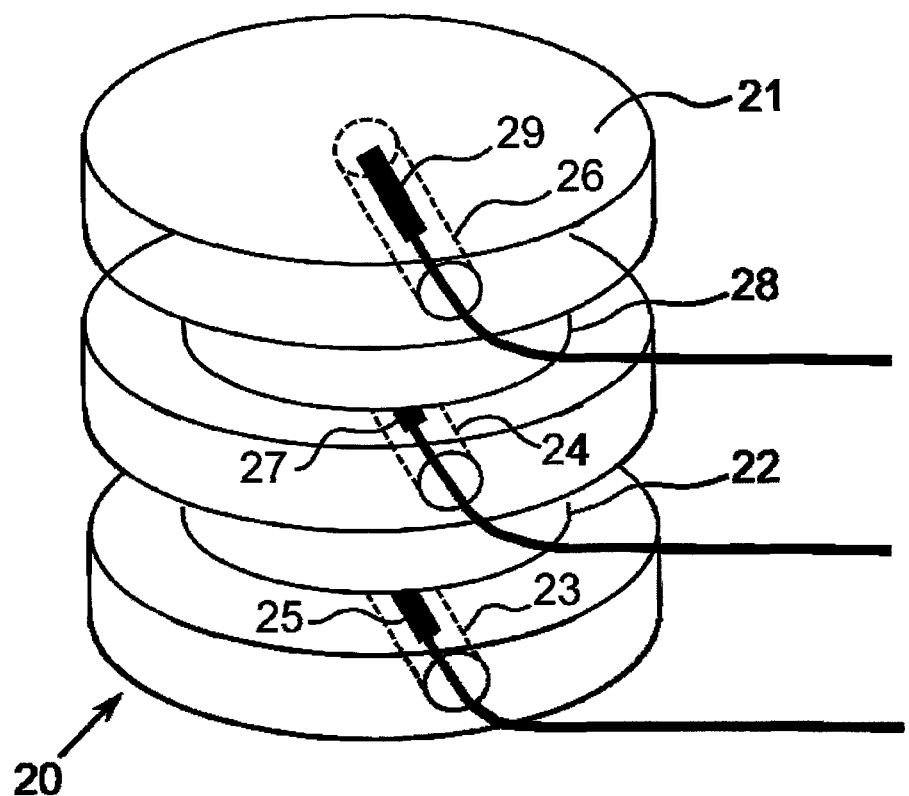
FIG. 3 is a schematic perspective and partially sectional view showing a second embodiment of the temperature-measuring device according to the invention.

FIG. 3 illustrates a second temperature-measuring device 20, in which a cylindrical insulator 21 is provided with rotationally symmetrical recesses 22, 28. Recesses 22, 28 are located between mounting holes 23, 24, 26 for first temperature sensor 25, second temperature sensor 27 and third temperature sensor 29. The heat transfer coefficient of the material between the temperature sensors 25, 27, 29 decreases due to the recesses 22, 28, which bring about a fitting of the insulator.

Predetermined heat transfer coefficients can be set by selecting different depths for the recesses. In addition, the lateral heat fluxes due to energy loss decrease.

Figure 4:
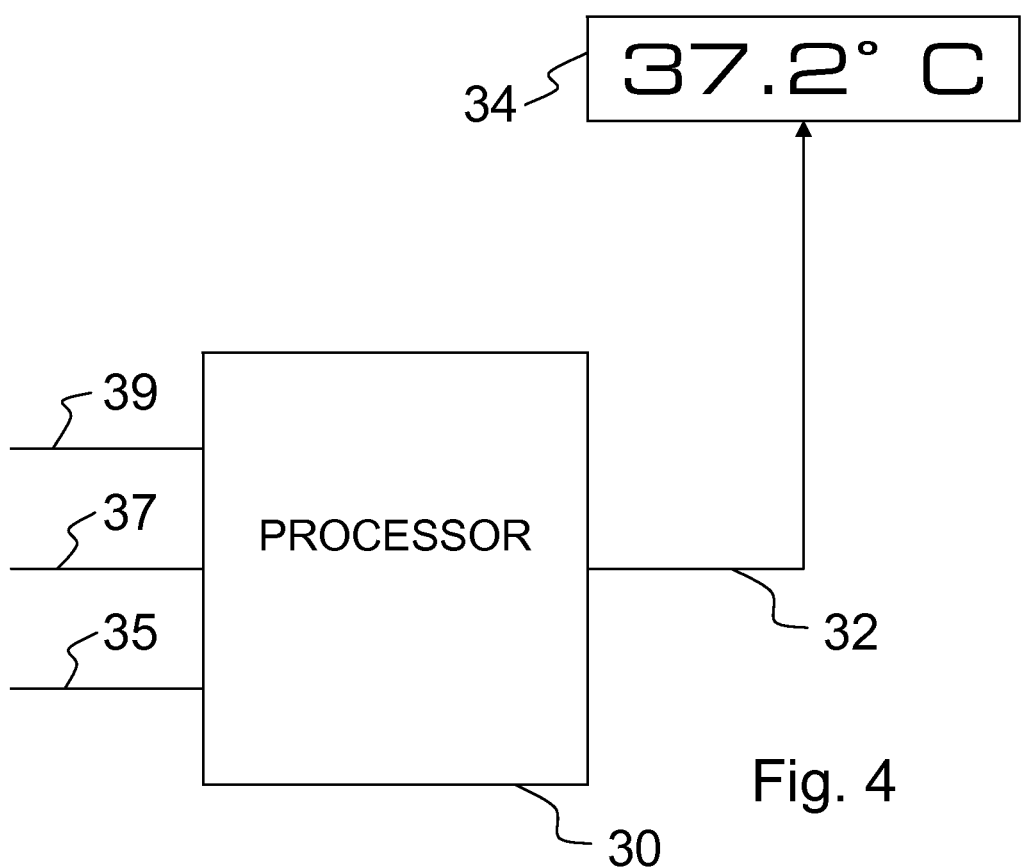
FIG. 4 is a schematic view showing a connected processor and display for either the first embodiment or the second embodiment of the temperature-measuring device according to the invention.

FIG. 4 shows a processor 30 and a display 34 that may be part of the first temperature-measuring device 10 and the second temperature-measuring device 20. The signal lines 35, 37 and 39 are respectively connected to the first temperature sensor 15, the second temperature sensor 17 and the third temperature sensor 19 of the first temperature-measuring device 10 or are respectively connected to the first temperature sensor 25, the second temperature sensor 27 and the third temperature sensor 29 of the second temperature-measuring device 20. The processor 30 receives temperature signals from each of the first temperature sensor, the second temperature sensor and the third temperature sensor and provides a body core temperature $T_{core}$ by assuming a constant ratio of lateral heat fluxes $Q5/Q4=\alpha$ at the insulator between the first temperature sensor and the second temperature sensor and between the second temperature sensor and the third temperature sensor. The a body core temperature $T_{core}$ is obtained (calculated) by the processor 30 from the relationship described by the formula $$T_{core} = T_1 \cdot \left[1 + \frac{k_s}{k_g}\left(1 + \frac{1}{\alpha}\right)\right] - T_2 \cdot \left(\frac{k_s}{k_g} + \frac{k_s + k_t}{\alpha k_g}\right) + T_3 \cdot \frac{k_t}{\alpha k_g}$$

in which
$k_g$=heat transfer coefficient of tissue of the living being, and
$k_s$, $k_t$=heat transfer coefficients of the insulator between the first temperature sensor and the second temperature sensor and between the second temperature sensor and the third temperature sensor. The obtained body core temperature $T_{core}$ may then be provided to the display 34 connected via line 32 to the processor 30, for display of a value of the body core temperature $T_{core}$ provided by the processor 30.

While specific embodiments of the invention have been shown and described in detail to illustrate the application of the principles of the invention, it will be understood that the invention may be embodied otherwise without departing from such principles.

LIST OF REFERENCE NUMBERS

1 Temperature-measuring device
2, 12 Body tissue
3 First double temperature sensor
4 Second double temperature sensor
5, 15, 25 First temperature sensor
6 First insulator
7, 17, 27 Second temperature sensor
8 Second insulator
9, 19, 29 Third temperature sensor
10 First temperature-measuring device
11, 12 Cylindrical insulator
13, 14, 16 Mounting hole
23, 24, 26
20 Second temperature-measuring device
22, 28 Recess
$Q_1, Q_2, Q_3$ Main heat flux
$Q_4, Q_5$ Lateral heat flux

What is claimed is:

1. A device for determining the body core temperature of a living being, the device comprising:
a first temperature sensor for contact with the body surface for detecting skin temperature $T_1$,
an insulator for receiving said first temperature sensor;
a second temperature sensor at said insulator for detecting a temperature $T_2$ in an area of the main heat flux directed from the body surface into said insulator;
a third temperature sensor arranged opposite said first temperature sensor at said insulator, wherein assuming a constant ratio of lateral heat fluxes Q5/Q4=α at said insulator between said first temperature sensor and said second temperature sensor and said second temperature sensor and said third temperature sensor, the body core temperature $T_{core}$ is obtained from the relationship described by the formula:

$$T_{core} = T_1 \cdot \left[1 + \frac{k_s}{k_g}\left(1 + \frac{1}{\alpha}\right)\right] - T_2 \cdot \left(\frac{k_s}{k_g} + \frac{k_s + k_t}{\alpha k_g}\right) + T_3 \cdot \frac{k_t}{\alpha k_g}$$

in which
$k_g$=heat transfer coefficient of the tissue of the living being, and
$k_s, k_t$=heat transfer coefficients of said insulator between said first temperature sensor and the second temperature sensor and between the second temperature sensor and the third temperature sensor.

2. A device in accordance with claim 1, wherein said insulator is a homogeneous body with mounting holes, each of said mounting holes receiving a respective one of said temperature sensors, one of said mounting holes being arranged between another one of said mounting holes and yet another one of said mounting holes.

3. A device in accordance with claim 2, further comprising a processing device receiving temperature signals from each of said first temperature sensor, said second temperature sensor and said third temperature sensor and providing the body core temperature $T_{core}$ obtained from said relationship described by said formula, each of said mounting holes being aligned with one another with respect to an axial direction of said insulator.

4. A device in accordance with claim 3, wherein said insulator comprises a cylindrical insulator, said cylindrical insulator comprising rotationally symmetrical recesses, one of said rotationally symmetrical recesses being located between said one of said mounting holes and said another one of said mounting holes, wherein another one of said rotationally symmetrical recesses is located between said one of said mounting holes and said yet another one of said mounting holes.

5. A process for determining a body core temperature of a living being, the process comprising the steps of:
providing a measuring device, which has temperature sensors on both sides of an insulator for detecting a temperature $T_1$ near the body and a temperature $T_3$ away from the body, and a temperature sensor within the insulator for detecting a temperature $T_2$, wherein a main heat flux from the body tissue into the insulator extends from the temperature sensor near the body to the temperature sensor located away from the body and lateral heat fluxes of the insulator are present between the temperature sensors;
arranging the temperature sensor for detecting the temperature $T_2$ in the area of the main heat flux within the insulator between the outer temperature sensors near the body and away from the body;
assuming a constant ratio of the lateral heat fluxes Q5/Q4=α between two adjacent temperature sensors;
determining the body core temperature $T_{core}$ from the relationship described by the formula $$T_{core} = T_1 \cdot \left[1 + \frac{k_s}{k_g}\left(1 + \frac{1}{\alpha}\right)\right] - T_2 \cdot \left(\frac{k_s}{k_g} + \frac{k_s + k_t}{\alpha k_g}\right) + T_3 \cdot \frac{k_t}{\alpha k_g}$$

in which $k_g$=heat transfer coefficient of the tissue and $k_s, k_t$=heat transfer coefficients of the insulator between the temperature sensors.

6. A process in accordance with claim 5 wherein said insulator is a homogeneous body with mounting holes, each of said mounting holes receiving a respective one of said temperature sensors, one of said mounting holes being arranged between another one of said mounting holes and yet another one of said mounting holes.

7. A process in accordance with claim 6, further comprising providing the measuring device with a processing device receiving temperature signals from each of said first temperature sensor, said second temperature sensor and said third temperature sensor and providing the body core temperature $T_{core}$ obtained from said relationship described by said formula, each of said mounting holes being aligned with one another in an axial direction of said insulator.

8. A process in accordance with claim 7, wherein said insulator comprises a cylindrical insulator, said cylindrical insulator comprising rotationally symmetrical recesses, one of said rotationally symmetrical recesses being located between said one of said mounting holes and said another one of said mounting holes, wherein another one of said rotationally symmetrical recesses is located between said one of said mounting holes and said yet another one of said mounting holes.

9. A device for determining the body core temperature of a living being, the device comprising:
- an insulator having three spaced apart regions, each of said regions for receiving a temperature sensor;
- a first temperature sensor connected to said insulator at one of said three spaced apart regions for contact with a body surface of the living being for detecting a skin temperature $T_1$;
- a second temperature sensor connected to said insulator at another of said three spaced apart regions for detecting a temperature $T_2$ in an area of main heat flux directed from the body surface into said insulator;
- a third temperature sensor connected to said insulator at a further one of said three spaced apart regions and arranged opposite said first temperature sensor, with said second temperature sensor positioned between said first temperature sensor and said third temperature sensor; and
- a processing device receiving temperature signals from each of said first temperature sensor, said second temperature sensor and said third temperature sensor and providing a body core temperature $T_{core}$ by assuming a constant ratio of lateral heat fluxes $Q5/Q4 = \alpha$ at said insulator between said first temperature sensor and said second temperature sensor and between said second temperature sensor and said third temperature sensor, obtained from the relationship described by the formula $$T_{core} = T_1 \cdot \left[1 + \frac{k_s}{k_g}\left(1 + \frac{1}{\alpha}\right)\right] - T_2 \cdot \left(\frac{k_s}{k_g} + \frac{k_s + k_t}{\alpha k_g}\right) + T_3 \cdot \frac{k_t}{\alpha k_g}$$

in which
$k_g$=heat transfer coefficient of tissue of the living being, and
$k_s$, $k_t$=heat transfer coefficients of said insulator between said first temperature sensor and said second temperature sensor and between said second temperature sensor and said third temperature sensor.

10. A device in accordance with claim 9, wherein said insulator is a homogeneous body with mounting holes, each of said mounting holes receiving a respective one of said temperature sensors, one of said mounting holes being arranged between another one of said mounting holes and yet another one of said mounting holes.

11. A device in accordance with claim 10, further comprising a display connected to said processor for display of a value of the body core temperature $T_{core}$ provided by said processor, each of said mounting holes being aligned with one another in an axial direction of said insulator.

12. A device in accordance with claim 11, wherein said insulator comprises a cylindrical insulator, said cylindrical insulator comprising rotationally symmetrical recesses, one of said rotationally symmetrical recesses being located between said one of said mounting holes and said another one of said mounting holes, wherein another one of said rotationally symmetrical recesses is located between said one of said mounting holes and said yet another one of said mounting holes.

* * * * *